(12) United States Patent
Fitz et al.

(10) Patent No.: US 11,737,770 B2
(45) Date of Patent: Aug. 29, 2023

(54) CLOT RETRIEVAL

(71) Applicant: MicroVention, Inc., Aliso Viejo, CA (US)

(72) Inventors: Matthew J. Fitz, Vista, CA (US); Hussain Rangwala, Villa Park, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 210 days.

(21) Appl. No.: 16/888,073

(22) Filed: May 29, 2020

(65) Prior Publication Data

US 2020/0375616 A1    Dec. 3, 2020

Related U.S. Application Data

(60) Provisional application No. 62/873,529, filed on Jul. 12, 2019, provisional application No. 62/856,664, filed on Jun. 3, 2019, provisional application No. 62/855,510, filed on May 31, 2019.

(51) Int. Cl.
*A61B 17/221* (2006.01)
*A61B 90/00* (2016.01)

(52) U.S. Cl.
CPC ............ *A61B 17/221* (2013.01); *A61B 90/39* (2016.02); *A61B 2017/2217* (2013.01); *A61B 2090/3966* (2016.02)

(58) Field of Classification Search
CPC .......... A61B 17/221; A61B 2017/2212; A61B 2017/2217; A61B 2017/320024; A61B 2017/320775; A61M 2025/1075; A61M 25/1027; A61M 25/1029
See application file for complete search history.

(56) References Cited

U.S. PATENT DOCUMENTS

| | | |
|---|---|---|
| 7,094,249 B1 | 8/2006 | Broome et al. |
| 8,545,447 B2 | 10/2013 | Demarais et al. |
| 2008/0103516 A1* | 5/2008 | Wulfman ............ A61B 17/3207 606/180 |
| 2009/0038752 A1* | 2/2009 | Weng ................. A61M 25/1029 604/103.09 |
| 2012/0109057 A1* | 5/2012 | Krolik ................. A61M 25/10 604/103.01 |
| 2016/0038174 A1* | 2/2016 | Bruzzi ............ A61B 17/320725 606/159 |
| 2016/0058459 A1 | 3/2016 | Bowman |
| 2019/0110805 A1* | 4/2019 | Ulm, III ........... A61B 17/12172 |

FOREIGN PATENT DOCUMENTS

WO    WO2019/079296 A1    4/2019

OTHER PUBLICATIONS

WIPO, U.S. International Search Authority, International Search Report and Written Opinion dated Sep. 2, 2020 in International Patent Application No. PCT/US2020/035322, 9 pages.

* cited by examiner

*Primary Examiner* — Wade Miles
(74) *Attorney, Agent, or Firm* — Inskeep IP Group, Inc.

(57) ABSTRACT

A clot retrieval device is disclosed. In some embodiments, the device utilizes augmented radiopacity to improve imaging, an internal tensioning member, a plurality of connected components useful to engage larger clots, and/or a distal end configuration designed to enhance clot retention.

21 Claims, 10 Drawing Sheets

CLOT RETRIEVAL

RELATED APPLICATIONS

This application claims priority to U.S. Provisional Application Ser. No. 62/855,510 filed May 31, 2019 entitled Matter Removal System, 62/856,664 filed Jun. 3, 2019 entitled Matter Removal System, 62/873,529 filed Jul. 12, 2019 entitled Matter Removal System, all of which are hereby incorporated by reference in their entireties.

BACKGROUND OF THE INVENTION

Formation of thrombus in the vasculature can lead to clots over time, putting a patient at risk of ischemic stroke. There are a variety of techniques to remove clots, including aspiration and mechanical thrombectomy. The latter technique involves utilizing a mechanical device to grip and withdraw the clot. These mechanical devices are often referred to as clot retrieval devices or stentrievers—the latter term is often used since the devices were originally construed as stents reconfigured for clot retrieval purposes. Many clot retrieval or stentriever devices have a distally open configuration (e.g., like a stent) to enable the devices to grip and remove clots from the vasculature.

There are a number of issues with using traditional mechanical thrombectomy devices. Visualization of the thrombectomy device is important to ensure the device is appropriately positioned relative to the clot in order to capture the clot. However, it can be difficult to design a fully imageable radiopaque thrombectomy device since radiopaque materials are often difficult to work with.

Proper opening of a thrombectomy device can also be difficult, especially in the smaller vasculature regions of the brain. Thrombectomy devices typically utilize a shape memory material, and this shape memory property is responsible for device expansion upon release from a delivery catheter. However, as the devices are sized bigger or longer (e.g., to capture larger clots), and/or as the devices are utilized in smaller vessels thereby augmenting the resistance from the vessel wall, it can be difficult to get the thrombectomy device to expand completely, thereby negatively affecting clot capturing capability.

Additionally, the traditional open distal-end design of many thrombectomy devices or stentrievers can result in thrombus or clot shearing off and being thrown distally into the bloodstream during the retrieval procedure. This can result in clot or thrombus formation in other regions of the vasculature.

There is a need for a thrombectomy device which addresses these and other shortcomings.

SUMMARY OF THE INVENTION

A mechanical clot or thrombus retrieval device is described. The retrieval device can be considered as a thrombectomy device or stentriever.

In some embodiments, a retrieval device with enhanced opening characteristics is described. In one embodiment, a coil or spring element is used along an interior length region of a retrieval device and helps to ensure proper opening or expansion of the retrieval device. In one embodiment, a coil or spring element is used along an interior length region of a retrieval device and helps to ensure proper collapse of the retrieval device. In one embodiment, the coil or spring element is radiopaque to aid in visualization of the device.

In some embodiments, a retrieval device with a closed distal shape is described. In one embodiment, a retrieval device utilizes one or more tubular or cylindrically shaped elements with a closed-end configuration.

In some embodiments, methods of manufacturing a retrieval device is described. In one embodiment, a tubular or cylindrically shaped element with a closed-end configuration is manufactured. One or more of these components are connected together in order to manufacture a retrieval device.

In some embodiments, a retrieval device with at least a partially closed distal shape is described. A distal end of the clot retrieval device includes a plurality of radial segments where at least some of the radial segments are inwardly oriented in order to create a distal radial constriction, useful in trapping thrombus.

In one embodiment, a method of manufacturing a clot retrieval device is described. A tubular or cylindrically shaped element is created with an open distal end configuration, and a plurality of radial segments. At least some of these radial segments are then oriented radially inward in order to create a distal radial constriction.

In some embodiments, a retrieval device with radiopaque properties useful for imaging of the device is described. In one embodiment, a radiopaque spring element is used along an interior length region of a retrieval device. The radiopaque spring element can have additional benefits, such as helping to ensure proper opening and/or collapse of the device. In one embodiment, a radiopaque plating or marker component is added to selective areas of a retrieval device. In one embodiment, a tubular spiral radiopaque element is used on selective areas of a retrieval device. In one embodiment, a radiopaque coiled element is used on selective areas of a retrieval device. In one embodiment, a retrieval device has one or more coining holes which are filled with a radiopaque element.

In some embodiments, methods of manufacturing a retrieval device is described. In one embodiment, a plating or marker component is placed over selective regions of a retrieval device. In one embodiment, a tubular spiral radiopaque element is placed over selective regions of a retrieval device. In one embodiment, a retrieval device is manufactured with one or more coining holes and radiopaque material is filled into the coining holes. In one embodiment, a spring component is placed within an interior region of a retrieval device—in one embodiment, the spring component is radiopaque.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
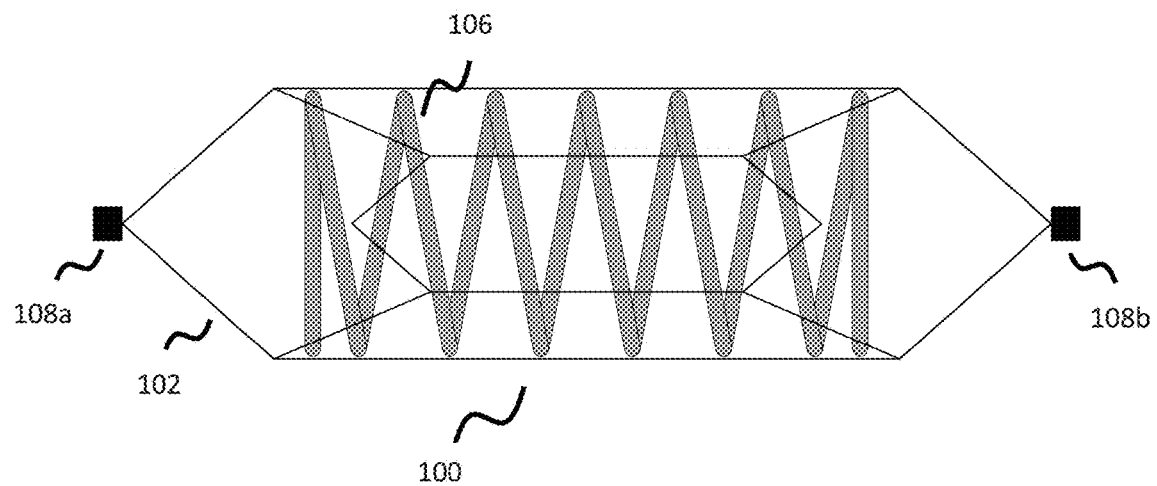
FIG. 1A shows a clot retrieval device utilizing a coil or spring element, according to one embodiment.

Mechanical retrieval, thrombectomy, and stentriever devices were discussed in the background section above and are useful for physically grasping and withdrawing the clot or thrombus from the vasculature. For the purposes of this specification, removal device, retrieval device, thrombectomy device, and stentriever shall be used interchangeably and shall generally refer to the same concept of a mechanical retrieval device used to grasp and remove clot or thrombus from the vasculature. Clot and thrombus shall also be used interchangeably.

The device embodiments described herein can be used to capture and/or retrieve clot, thrombus, as well as foreign body objects. Foreign body objects include elements that are not natural to the vasculature space, such as medical devices. One example is an embolic coil which may be used to occlude an aneurysm but may migrate from the aneurysm to another area of the vasculature, thereby creating a clot risk.

The current state of the art of these devices suffer from a number of shortfalls. One issue is proper visualization of the devices. Radiopaque components can be used to make a device viewable during a procedure, and it is desirable to visualize a substantial or an entire length of a thrombectomy device in order to ensure the device is sufficiently positioned with respect to the clot or thrombus to enable its capture. However, it can be difficult to make a retrieval device that is sufficiently radiopaque (and therefore imageable) along all or most of the device. One way would be to make the entire device of a metallic radiopaque substance (e.g., tantalum, palladium, platinum, or gold). However, these radiopaque materials exhibit poor shape memory properties, and good shape memory characteristics are needed to ensure the device properly collapses into its delivery state when within a catheter, and then expands to its natural expansion state when released from the catheter. Also, these radiopaque materials are typically expensive and create an economic challenge in developing a cost-effective retrieval device.

Ensuring proper opening of the thrombectomy device is important to ensure the device is completely opened to capture any clot or thrombus. Though a shape memory material (e.g., nitinol) can be used to create a thrombectomy device, it can still be difficult for the device to sufficiently expand under certain conditions—such as along a tortuous section of the vasculature, or within smaller blood vessels (e.g., those in the neurovasculature). Neurovasculature vessels, in particular, can be very small and tortuous making clot removal difficult in these areas. Other characteristics including but not limited to size of the blood vessel, device design (e.g., sizing in comparison to the vessel, thickness of the device, material selection) can contribute to difficulties in a thrombectomy device sufficiently expanding within the vasculature.

The following embodiments address these issues by providing a radiopaque imageable device which also has enhanced opening and/or closing characteristics to make a more usable thrombectomy device.

FIG. 1a illustrates a device 100 according to one embodiment utilizing a coiled or spring element 106. Device 100 includes a number of structural struts 102 extending along all or a portion of the device. These struts 102 define the outer perimeter of device 100, such that any clot or thrombus may initially contact the struts 102 during a clot retrieval procedure and then be enclosed partially or completely within the area of the struts 102 during the retrieval procedure. The struts 102 in their aggregate extend from one end of the device 100 to the other end and thus span the entire length of the device, although struts 102 may be composed of various strut segments spanning various lengths of the device which, which, in their aggregate, span the entirety of the device 100. In one embodiment, the device 100 (including struts 102) is composed of a shape memory metallic material, such as nitinol or stainless steel.

Device 100 includes proximal and distal terminal regions 108a, 108b. The proximal terminal region (e.g., 108a) is connected to an elongated delivery pusher (not shown)—and the pusher is gripped and pushed by a user to navigate the connected thrombectomy device 100 through a delivery catheter and to push the device 100 out of the delivery catheter and into the vascular treatment location.

Figure 1B:
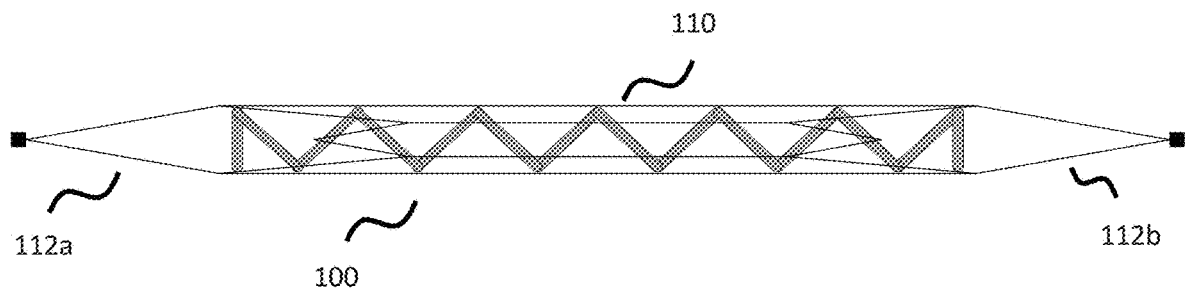
FIG. 1B shows the clot retrieval device of FIG. 1A in a radially collapsed and longitudinally expanded state, according to one embodiment.

FIG. 1a shows a device 100 in its radially expanded and longitudinally shortened configuration, which it adopts when not constrained within a delivery catheter. This is due to heat set, expansile shape memory that is built into the device 100 to allow the device 100 to adopt an expansile configuration when released from a delivery catheter. FIG. 1b shows the same device 100 in its radially constrained and longitudinally elongated configuration, which it adopts when within a delivery catheter (not shown).

In one embodiment terminal regions 108a, 108b are tubular radiopaque marker bands (e.g., tantalum, platinum, palladium, gold, or composite material like platinum-iridium) useful in visualizing the ends of device 100. In another embodiment, terminal regions 108a, 108b are thickened cylindrical regions utilizing similar material as the rest of the device 100 (e.g., shape memory metallic material). Terminal regions 108a,108b can either be solid such that there is no through-lumen therethrough, or alternatively can each include an inner hole or through-lumen.

As can be appreciated from FIGS. 1a and 1b (and particularly FIG. 1b which details these elements), thrombectomy device 100 has a device body comprising a cylindrical or tubular medial section 110, and tapered proximal and distal end sections 112a, 112b connected to medial section 110. The cylindrical or tubular medial section 110 represents a larger diameter section of device 100, while the tapered ends 112a and 112b represent smaller diameter end regions or sections of device 100. The tapered ends 112a, 112b are in turn connected to terminal regions 108a, 108b.

In one embodiment shown in FIGS. 1a-1b, coil or spring element 106 is connected directly to structural struts 102 along one or more locations along the struts 102 in order to attach the coil or spring element 106 to the struts 102 of device 100 (note: these attachment points are not explicitly shown in the Figures). This attachment can be done in a variety of ways, including via welding, adhesive, or mechanical retention elements (e.g., a wound coil, clip, or tubular band to provide interconnection). In one example, coil or spring element 106 is attached to struts 102 along or near a medial/middle section of the device 100, so as to provide the retention primarily along a center region of the device 100. In another example, the coil or spring element 106 is attached to struts 102 near proximal and distal ends of the device 100 (e.g., along the tapered end sections 112a, 112b) so as to provide retention primarily along both ends of device 100. In another example, coil or spring element 106 is attached along struts 102 located along a proximal, medial, and distal section of device 100 so as to provide retention along a substantial length of device 100.

Coil or spring 106 preferably spans an entirety or a majority of the length of the device 100, as shown in FIGS. 1a and 1b. In one preferred embodiment, coil or spring 106 is radiopaque, and is therefore visible through radiographic imaging techniques and will allow an associated length and diameter of thrombectomy device 100 (i.e., the length of the thrombectomy device associated with the radiopaque coil/spring 106) to be visible during the clot retrieval procedure. Radiopaque material such as tantalum, gold, platinum, palladium, or a composite material such as drawn-filled tubing with a radiopaque core and nitinol jacket can be used to create coil or spring 106. In another example, a good shape memory material such as nitinol or stainless steel is coated with a radiopaque material (such as the radiopaque materials outlined above) to create a radiopaque coil/spring 106 which also has strong shape memory properties. Where coil or spring 106 is radiopaque and extends along a majority of entirety of the device, this will help visualize most of all of the length of device 100, which is important in confirming proper placement relative of the thrombectomy device relative to a clot. In one example, coil or spring 106 extends at least through the tubular portion of device 100 (e.g., not necessarily through the tapered proximal and distal regions 112a, 112b—where these tapered end regions are shown in FIG. 1b), so that at least the tubular portion of the device which comprises the larger diameter region of the device is visible. Since coil or spring 106 spans an interior region of device 100, it can be considered as an inner element or an inner elongated element of device 100 which adopts a radially expanded and longitudinally shortened configuration (e.g., FIG. 1a) and a longitudinally elongated and radially compressed configuration (e.g., FIG. 1b).

Coil or spring 106 can be manufactured in a number of ways. In one example, a wire is wound around a cylindrical mandrel to create a plurality of adjacent windings. This shape is then optionally heat treated to establish an expanded, shape memory coil-like or spring-like shape. In this way, the coil or spring has this shape imprinted via shape memory, which further helps the coil or spring 106 adopt its nominal or expansile, non-elongated shape as the device 100 is delivered out from the delivery catheter. However, even if no such heat treatment is undertaken, the coil or spring 106 will have some degree of stored potential energy when device 100 is in its elongated, FIG. 1b shape (e.g., in a delivery catheter) due to the natural tendency of an object to resist deformation of its shape. Therefore, when device 100 is released from the delivery catheter, this stored energy will be released, causing coil or spring 106 to adopt its more expansile shape and in turn also helping propel device 100 into its expansile shape of FIG. 1a. This relationship is also mutual, as the built-in shape memory of device 100 will allow it to expand upon release from a delivery catheter (e.g., FIG. 1b shape) into its expansile (e.g., FIG. 1a) shape. Since the coil or spring 106 is connected to the device, it too will adopt its expansile shape as the device 100 adopts its expansile shape.

Coil or spring 106 adopts a radially expanded and longitudinally shortened shape when device 100 is in its radially expanded and longitudinally shortened shape, and a radially contracted and longitudinally elongated shape when device 100 is in its radially contracted and longitudinally elongated shape, as can be appreciated in the context of FIGS. 1a-1b. This occurs, at least, since the coil or spring 106 is connected to one or more strut portions 102 of the device 100, however, as will be explained later, the coil or spring 106 can be connected in various ways to the device 100 in various embodiments.

In one embodiment, similar to what is shown in FIG. 1a, when device 100 is in its expanded shape, coil or spring 106 is close or substantially flush with an inner surface of struts 102 (e.g., similar in diameter to the expanded shape diameter of device 100). One such advantage to this configuration is that imaging over an entire width or diameter of device 100 is possible due to the radiopacity of the coil or spring 106 and since the coil or spring 106 is substantially close to the struts 102 which define the periphery of device 100.

In one embodiment, coil or spring element 106 extends around an entire inner periphery of thrombectomy device 100 when the thrombectomy device is in its expanded shape (i.e., near or adjacent the struts 102 of the device 100, around an entire inner periphery of device 100). Such a configuration may offer some benefits in terms of providing a clear passage radially within device 100 for clot or thrombus retention. In some embodiments, coil or spring element 106 can utilize projecting components (e.g., barbs), or a chemical binding agent (e.g., a retentive coating) to help ensure any clot that contacts coil or spring element 106 is retained by the coil or spring element to augment clot retention of the device. Similarly, struts 102 can also utilize these retentive elements to help augment clot retention.

In one embodiment, coil or spring 106 adopts a substantially flat or linear shape when in its elongated configuration (meaning, when thrombectomy device 100 is in its elongated and radially collapsed configuration). In such a configuration, windings of coil or spring 106 would be sparsely spaced apart and limited in diameter so as to not be as noticeable (e.g., in comparison to its expanded, FIG. 1a shape). In another embodiment (e.g., shown in FIG. 1b), coil or spring 106, in its elongated configuration, is not completely substantially flat or linear and still has more of a traditional coil or spring-like shape with noticeable windings, even when extended or stretched.

In another embodiment, coil or spring element 106 assumes a less radially expansive configuration when device 100 is in its expanded state—such that coil or spring element 106 adopts an elongated configuration of FIG. 1b when collapsed, and a radially expanded configuration not substantially different from the elongated configuration. This configuration has some utility for a relatively radially small thrombectomy device 100 which does not radially expand to a significant degree when in its expanded configuration compared to its extended/radially collapsed/delivery configuration (e.g., its configuration when within a delivery catheter).

Wire diameter of coil or spring 106 (i.e., the diameter of the wire itself which is wound to create the coil or spring 106 shape) can vary depending on the desired performance characteristics. A thicker versus thinner wire diameter will affect force exerted against struts 102 (in an embodiment where coil or spring 106 is configured to contact the struts 102 in an expanded shape). A thicker versus thinner wire diameter will also potentially either resist or augment expansion as device 100 adopts its expanded shape—depending on other characteristics such as, for example, how and where the coil or spring 106 is attached to device 100 and the degree of tension coil or spring element 106 is under when in its elongated (e.g., FIG. 1b) configuration.

Figure 3A:
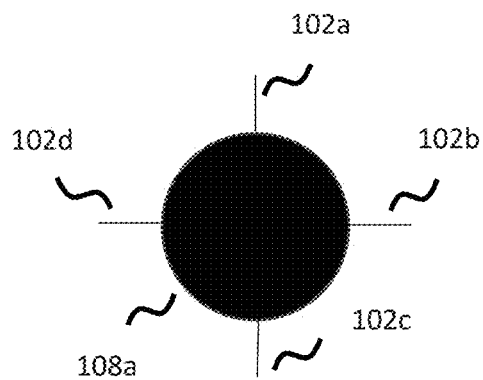
FIG. 3A shows an end region of a clot retrieval device, according to one embodiment.
Figure 3B:
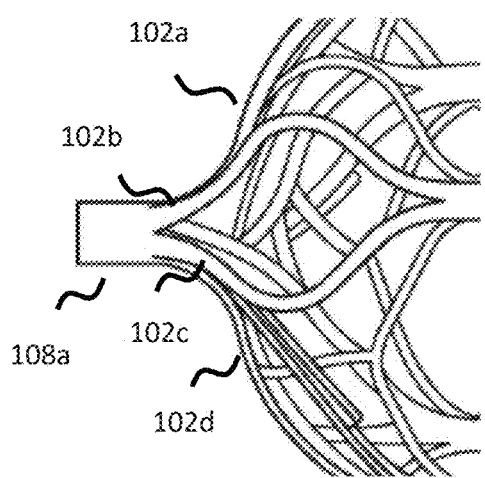
FIG. 3B shows an end region of a clot retrieval device, according to one embodiment.

Thrombectomy device 100 of FIGS. 1a and 1b has a closed, funneled, or tapered proximal and distal end shape (e.g., sections 112a, 112b, as discussed earlier). Traditional or prior art stentrievers generally have an open distal end shape, as discussed earlier. There are some disadvantages to this open distal end shape—mainly that it is relatively easy for clot to dislodge and escape from the distal end of the device during the retrieval procedure. This creates a risk of clot migrating elsewhere further downstream in the vasculature, just sending the clot from one location to another. One advantage of the embodiment is the closed distal end shape which helps prevent this issue. In practice, the struts will emanate from one terminal region 108a (e.g., at a proximal end of the device 100) and end at another terminal end region 108b (e.g., at a distal end of the device 100). Though device 100 is illustratively shown from its side profile view, a number of struts are configured to form the structure. Thus, by way of example, a plurality of struts (e.g., 2, 4, 6, 8, 10, or 12) radially project from element 108a. These struts can be connected at equidistant intervals around the circular shape, as shown in FIG. 3a where 4 struts 102a-102d emanate from terminal region 108a. This arrangement is shown from a different perspective in FIG. 3b, where struts 102a-102d extend from terminal region 108a. A similar number of struts terminate at opposing terminal region 108b. In between the two terminal end regions 108a, 108b, the struts can combine to form a condensed number of struts (e.g., a pair of the struts condense into one strut along a length of the device 100), or branch off to form a greater number of struts (e.g., a pair of the struts branch off into 4 struts, and then condense down into two struts near their termination at terminal region 108b)—this is shown in more detail in FIG. 3b where the struts condense and branch off along a length of a device. This can be useful to create a complex and varied strut shape especially in the middle of a thrombectomy device, which is the portion of the device most likely to contact clot or thrombus. Engagement or contact with the device struts 102 can help device 100 engage the clot or thrombus, and in this way having larger strut surface coverage can provide potential benefits in clot engagement and retrieval.

Figure 1C:
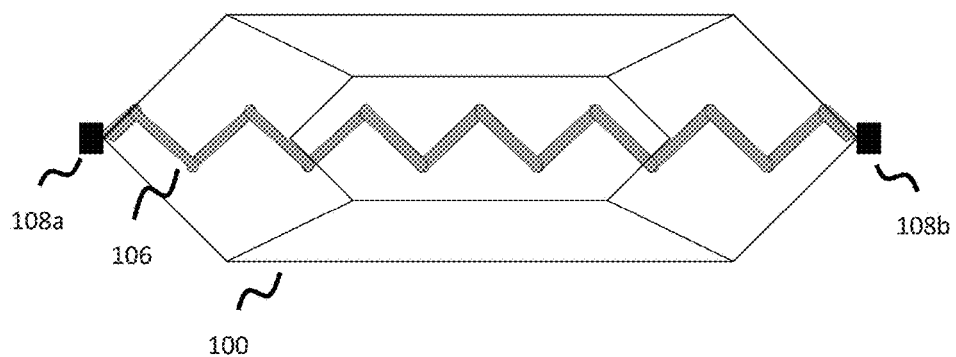
FIG. 1C shows a clot retrieval device utilizing a coil or spring element, according to another embodiment.
Figure 1D:
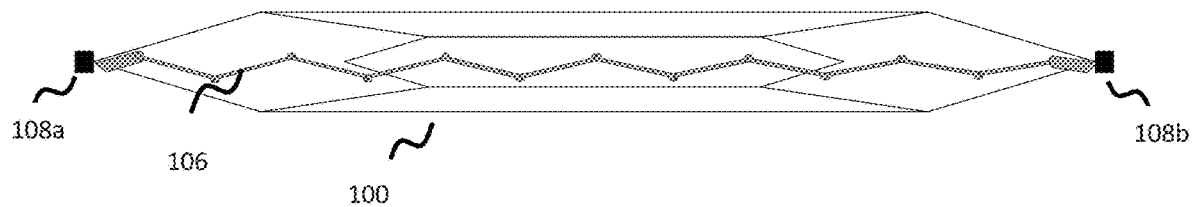
FIG. 1D shows the clot retrieval device of FIG. 1A in a radially collapsed and longitudinally expanded state, according to one embodiment.

Another embodiment, shown in FIGS. 1c and 1d, utilize a coil or spring 106 affixed at each end directly to terminal regions 108a and 108b of clot retrieval device 100 (e.g., via welding, adhesive, or mechanically through a screw interface). Since coil or spring 106 is connected directly to the terminal ends of the device 100, coil or spring 106 will automatically adopt an elongated configuration when device 100 is in an elongated and compressed state (e.g., in a delivery catheter), and then a shortened and radially expansile configuration when device 100 is in an expanded shape (e.g., upon being released from the delivery catheter). Optionally, coil or spring 106 can also be attached at one or more locations along the struts 102 of device 100 (similar with respect to the embodiments of FIGS. 1a and 1b, described earlier) to further augment attachment strength between coil or spring 106 and device 100. These additional attachment locations can also affect mechanical properties of the device (e.g., increased resistance to expansion or further augmenting expansion) and can therefore be used to further alter desired mechanical properties of device 100.

Coil or spring 106 can be affixed to a hole or through-lumen location of terminal end regions 108a, 108b (where those terminal regions utilize an inner hole or through-lumen). Alternatively, where terminal regions 108a, 108b are solid (i.e., having no such hole or through-lumen), coil or spring 106 can be directly attached to solid terminal regions 108a, 108b.

Figure 2A:
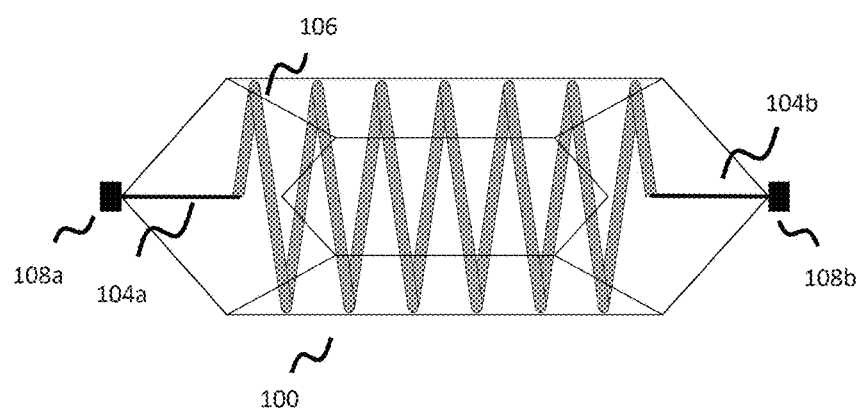
FIG. 2A shows a clot retrieval device utilizing a coil or spring element, according to another embodiment.
Figure 2B:
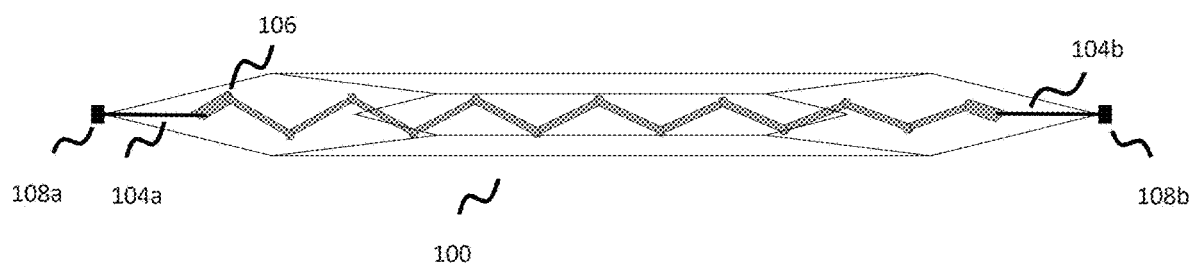
FIG. 2B shows the clot retrieval device of FIG. 2A in a radially collapsed and longitudinally expanded state, according to one embodiment.

FIGS. 2a-2b show another embodiment where a first elongated end element 104a is connected to terminal region 108a, and a second elongated end element 104b is connected to terminal region 108b. Elongated end elements 104a, 104b can either be a wire or tubular structure. Coil or spring 106 is connected to each elongated end element 104a, 104b (e.g., either at the most inwardly-facing location of each end element 104a, 104b or somewhere along each end element 104a, 104b). In this manner, coil or spring 106 is indirectly connected to each end of device 100, and in this manner coil or spring 106 expands as the device 100 expands, and elongates as device 100 elongates/adopts a compressed shape. Optionally, coil or spring 106 may also be connected at one or more strut locations 102 along the device 100.

End elements 104a, 104b can be affixed to a hole or through-lumen location of terminal regions 108a, 108b (where those terminal regions utilize an inner hole or through-lumen). Alternatively, where those terminal regions 108a, 108b are solid (i.e., having no such hole or through-lumen), elongated end elements 104a, 104b can be directly attached to solid terminal regions 108a, 108b.

Another similar embodiment (not pictured) can utilize a telescoping elongated element extending through the length of device 100 and connected to each terminal end region 108a, 108b. The telescoping nature of the elongated element allows it to extend and contract as the clot retrieval device, respectively, elongates and expands. In one embodiment, the telescoping element is radiopaque to allow the length of the device to be visualized. In one embodiment, a radiopaque coil or spring 106 is connected at one or more locations along the telescoping element to provide or augment imaging. Radiopaque coil or spring 106 may solely be connected to this telescoping elongated element, or can be connected to struts 102 of device 100, or can be connected to both the telescoping elongated element and struts 102 of device 100.

The configurations and explanations and different examples and embodiments of coil or spring 106 as described in the embodiments of FIGS. 1a-1b above generally apply to the embodiments of FIGS. 1c-1d, 2a-2b as well since only the mechanism of attachment between coil or spring 106 and device 100 is different. Therefore, the coil or spring 106 can be configured in a variety of ways regarding at least attachment to the device (e.g., whether or not attached to struts 102), degree of radial expansion and/or longitudinal elongation in an expanded vs collapsed configuration, degree to which the coil or spring is tensioned or utilizes shape memory to affect expansion and/or contraction of device 100, etc.

One advantage to a coil or spring shape for element 106 is that there is the ability to adopt more of a radially collapsed/stretched shape when elongated (e.g., see FIG. 1b, 1d, 2b). Coil or spring 106 will tend to store energy or be tensioned in this stretched configuration. The built-in potential energy along a coil or spring shape when tensioned or stretched can also help propel the device 100 into its expanded shape (e.g., see FIG. 1a, 1c, 2a) when the device 100 is released from a delivery catheter. This offers advantages in promoting proper opening of the device, for instance where device 100 is being deployed through tortuous anatomy or through a small blood vessel (e.g., in the neurovasculature) where there are many compressive forces surrounding the device 100. The stiffness or k-factor of coil/spring 106, length of coil or spring element 106, and the number of windings along coil or spring element 106 are all variables that can be tweaked in order to customize the mechanical properties of thrombectomy device 100. K-Factor is a component of Hooke's law which correlates the force needed to compress or elongate a spring with the distance of compression, represented as the letter "k" in the equation F=kx. K-factor (associated with spring stiffness) is a property of the material used as well as the width and length of the wire used to create a coil or spring 106. In one preferred example discussed earlier, coil or spring 106 is composed of radiopaque materials (specific examples mentioned earlier), though other examples can utilize traditional shape memory materials such as nitinol or stainless steel—all these materials will have different k or stiffness values—thus the material can be specifically selected to generate a desired k or stiffness profile. Similarly, the length and/or the diameter of the wire used in shaping coil or spring 106 can be adjusted to affect the stiffness characteristics of the coil or spring (and thus, the k-factor). These properties can also affect how much, if any, resistance coil or spring 106 provides to elongation (e.g., when a thrombectomy device is being collapsed upon placement into a delivery catheter). These properties can also affect how much coil or spring 106 helps either urge expansion into a radially expanded shape, or resists such expansion. The number of attachment points and attachment locations between coil or spring 106 and the rest of device 100 (e.g., where and how they are attached, whether and where they are attached along the struts 102, etc.) can also affect how coil or spring 106 affects device 100 as device 100 radially expands or longitudinally elongates.

One advantage of a configuration where a coil/spring 106 is located substantially near or adjacent struts 102 when in its expanded state (whether directly attached to struts 102 or not) is that coil/spring 106 can be used to apply outward force against the struts to help prop open the struts 102 as the device 100 adopts its expanded configuration—especially in a scenario where a coil/spring 106 is tensioned and therefore has some degree of imparted potential energy in its compressed and elongated state which is released upon deployment. In other words, upon release from a delivery catheter, the built-in shape-memory of the device along with the force/tension integral to coil/spring 106 will expand coil/spring 106, in turn aiding in the expansion of the overall device 100. In this way, in some embodiments coil or spring 106 can be considered as a tensioning member. In a similar way as to how tensioning coil/spring 106 can augment expansion of device 100, imparting shape memory into coil or spring 106 may provide a similar benefit.

The various embodiments presented thus far may utilize different attachment mechanisms between coil or spring element 106 and device 100 which can impact how coil/spring element 106 affects the device 100. For instance, in the context of FIGS. 1a-1b, coil or spring 106 is directly affixed to one or more struts 102 of the device 100. In this example, the radial expansion of struts 102 after delivery will in turn affect the radial expansion of coil or spring 106. However, since coil or spring 106 is likely tensioned or otherwise storing energy in its collapsed state (e.g., in the FIG. 1b configuration), coil or spring 106 will also exert force against struts 102 during expansion. Similarly, if coil or spring 106 has shape memory imparted, this shape memory will cause the coil or spring 106 to exert force against struts 102 as coil or spring 106 adopts its own heat-set expansile shape.

In the context of FIGS. 1c-1d where the coil or spring 106 is attached, at least, to each end of device 100, the heat set expansion of device 100 will cause coil or spring 106 adopt its own expanded shape (e.g., see FIG. 1c). However, since coil or spring 106 is naturally tensioned in its elongated, FIG. 1d shape or otherwise stores energy (e.g., due to imparted shape memory), the release of this energy upon expansion will also impact the shape of the device 100 and may help it adopt its radially expansile shape of FIG. 1c. This relationship is similar in the context of FIGS. 2a-2b, where coil or spring 106 is attached to both ends of device 100 via linkage with elongated end elements 104a, 104b. Additional attachment of coil or spring 106 to the strut elements 102 of device 100 will only enhance the physical connection and the associated interplay between coil or spring 106 and the rest of device 100.

The embodiments shown and described herein and with respect to FIGS. 1a-2b, can utilize additional features. For instance, a plurality of coils or springs 106 utilizing one or more of the attachment parameters shown and described above can be utilized. Furthermore, coil or spring 106 itself, in an alternative configuration, can be composed of a series of connected coils or springs connected together along its length to create a complete coil or spring structure.

Thrombectomy devices are typically configured as a single element (e.g., a single tubular element) which is used to engage a clot. While this can be suitable for smaller clots, it can be difficult to use such a design to engage a larger or longer clot, which can span beyond the length of a single tubular element. The following embodiments address this issue by utilizing a plurality of clot engaging elements, which can offer benefits in retrieving larger clots.

Figure 4:
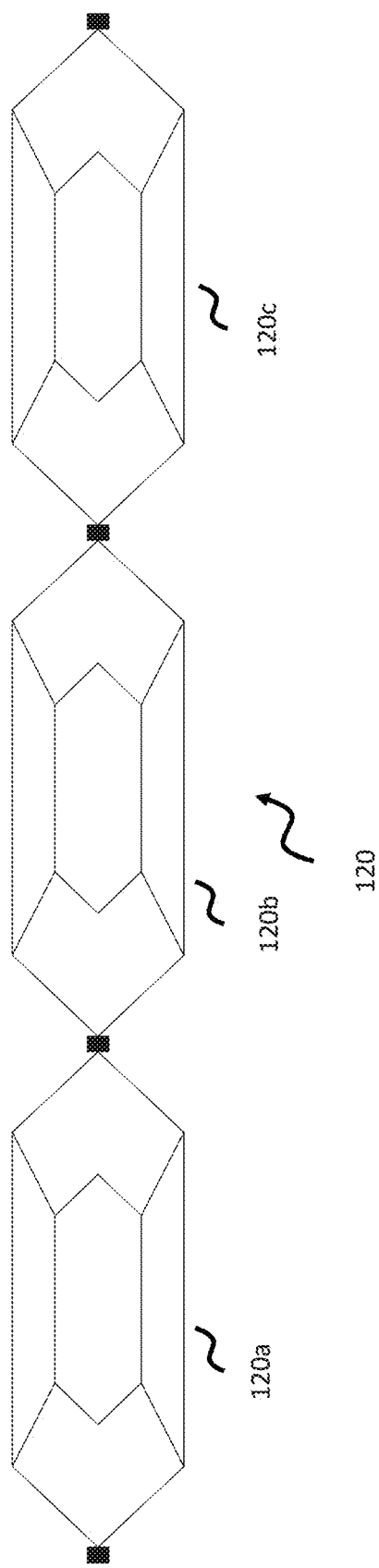
FIG. 4 shows a clot retrieval device having a plurality of connected components, according to one embodiment.

FIG. 4 illustrates a thrombectomy device 120 according to one embodiment, utilizing a plurality of thrombectomy components 120a-120c. Three components 120a-120c are shown illustratively, but in other embodiments fewer (e.g., 2) or more (e.g., 4-10) components can be used along the device 120. Each thrombectomy component 120a, 120b, 120c is configured as its own mechanical capture object, where these components are connected in order to create an elongated device 120, which is longer than the component objects 120a-120c. Each thrombectomy component 120a-120c can be considered as its own device body, thereby the device 120 has a plurality of connected device bodies.

Figure 5:
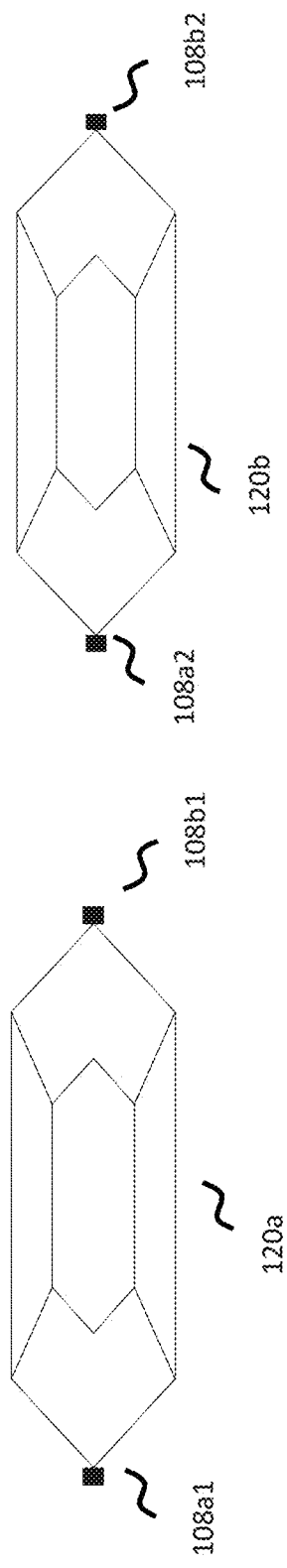
FIG. 5 shows the clot retrieval device of FIG. 4 wherein end regions of each component are visible, according to one embodiment.

The thrombectomy components 120a-120c can be connected together in various ways. Two separated component 120a, 120b are shown in FIG. 5. Each component has a proximal terminal region and a distal terminal region at either end of the component, these terminal end regions are configured similarly to the end regions described in the embodiments for FIGS. 1-3b. In this way, component 120a has a proximal terminal region 108a1 and a distal terminal region 108b1 and component 120b has a proximal terminal region 108a2 and a distal terminal region 108b2.

In the context of FIGS. 4 and 5, the "left" side of the Figures can be thought of as representing a proximal part of the device 120, while the "right" side of the Figures represent a distal part of the device 120. In this way, the right side (e.g., the right-most component 120c) will be the first one deployed into the vasculature. An end region of one thrombectomy component 120a is linked to an adjacent end region of the next thrombectomy component such that the components become linked to create the elongate device 120. In the context of FIG. 5, terminal end region 108b1 is linked to an adjacent terminal end region 108a2. Where more components are added (as shown in FIG. 4), this linking continues along the length of the device 120.

In one example, one end region of a thrombectomy component is welded to an adjacent end region of an adjacent thrombectomy component to link all the thrombectomy components 120a-120c of device 120 together. In another example, a linking rod or pin with flared ends is placed within the radius of the two adjacent terminal regions (e.g., element 108b1 and 108a2) such that the two thrombectomy components are thereby linked. This linking rod or pin comprises a tubular medial section smaller than an internal diameter of the end region (i.e. smaller than an internal passage that passes through terminal end regions 108b1 and 108a2) but the ends of this rod or pink are larger than the diameter of the internal passage to retain the link/pin within between two of the thrombectomy components (e.g., one linking pin between components 120a and 120b, and another linking pin between components 120b and 120c). This design, as well as other thrombectomy device embodiments, is discussed in more detail in U.S. Pat. No. 9,211,132 which is hereby incorporated by reference in its entirety. The use of a linking pin would necessitate the use of a terminal region (e.g., elements 108b1, 108a2) which each utilize an inner hole or through-lumen to allow passage of the link.

The attachment method between the thrombectomy component can affect the design and functionality of thrombectomy/clot retrieval device 120. For instance, welding the ends together will attach the components 120a-120c in a manner so as to preclude independent rotation of one component (e.g., component 120a) relative to another (e.g., component 120b). However, a linking pin concept as discussed earlier will enable independent rotation of each component 120a-120c. This is because rather than being directly attached to each other, the components are individually linked in pairs through a linking pin. This offers advantages in certain operative situations. For instance, where a clot is located along a tortuous bend of the vasculature and independent rotation of each component can allow the device to shear clot off the vasculature wall to aid in its capture.

In other embodiments, various attachment methods or techniques can be combined. For instance, some thrombectomy components can be linked together via the linking pin concept, and other thrombectomy components can be linked together via welding or other direct attachment. For instance, components 120b and 120c can be linked together via the linking pin concept which allows component 120c to rotate independently of component 120b. Components 120b and 120a can then be directly attached (e.g., welded) to each other, such that these components cannot independently rotate relative to each other. With this design, only component 120c can rotate independently of the other components 120a, 120b. This is just an illustrative example, and designs utilizing more components (e.g., more than three) can utilize various combinations of attachment to allow selective rotation of one or more components. In some embodiments, it may be more desirable to have independent rotation along one or more distally located components to help urge these components into secure engagement with the clot to aid in the retrieval process.

In another embodiment, the thrombectomy device which includes a plurality of thrombectomy components (e.g., 120a-120c) is created in a different manner rather than linking a plurality of separate components together. Instead, one contiguous elongated device 120 is created which is composed of a plurality of shapes (e.g., components 120a-120c). However, instead of the components being separately linked, the complete device itself is created over a tubular mandrel having a series of tubular sections and tapered sections in between to create a singular elongated element with a variable profile along its length. This configuration can offer some benefits in not requiring separate elements to be linked, and therefore having a contiguous structure.

The embodiments presented discussed thus far and presented in FIGS. 1-5 can be created in a variety of ways. In one example, a flat sheet of a shape memory metallic material (e.g., nitinol or stainless steel) is laser cut to create a flat sheet comprising a plurality of struts and gap or open regions in between the various struts. This shape as then heat set over a cylindrical mandrel to adopt a generally tubular configuration. The funneled or tapered proximal and distal end shapes can be created by utilizing a similar funneled or tapered mandrel shape which those specific sections are placed over. Alternatively, a tubular sheet material is laser cut to create the overall strut pattern utilized in the thrombectomy device. In this way, the thrombectomy device is already in its tubular shape prior to the laser cutting step.

Figure 6:
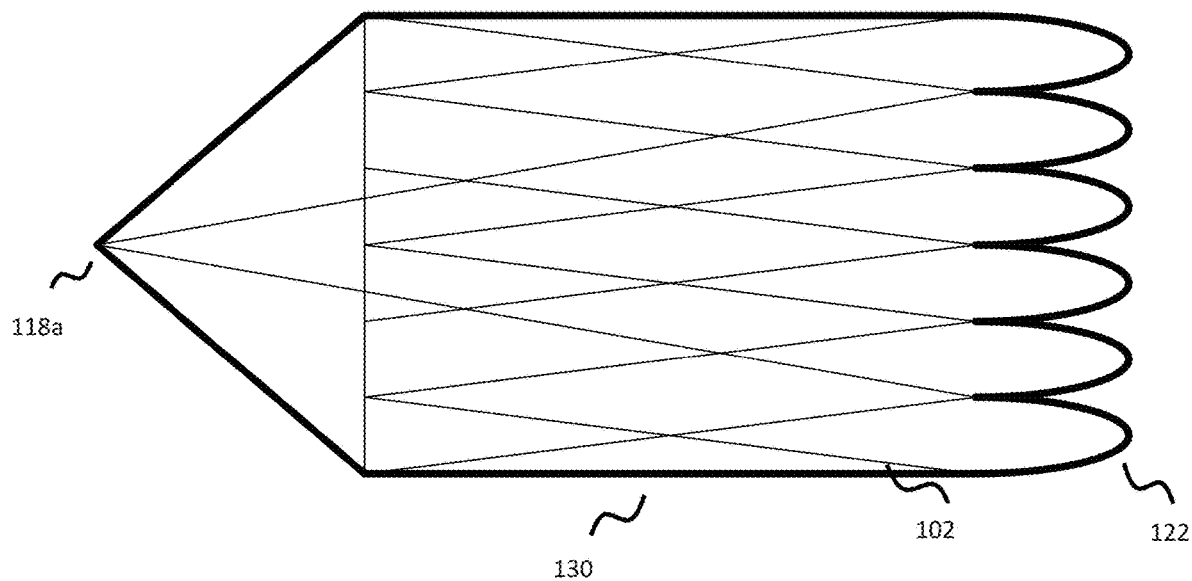
FIG. 6 shows a flattened configuration of a clot retrieval device, according to one embodiment.
Figure 7:
FIG. 7 shows the clot retrieval device of FIG. 6 in an assembled state, according to one embodiment.
Figure 8:
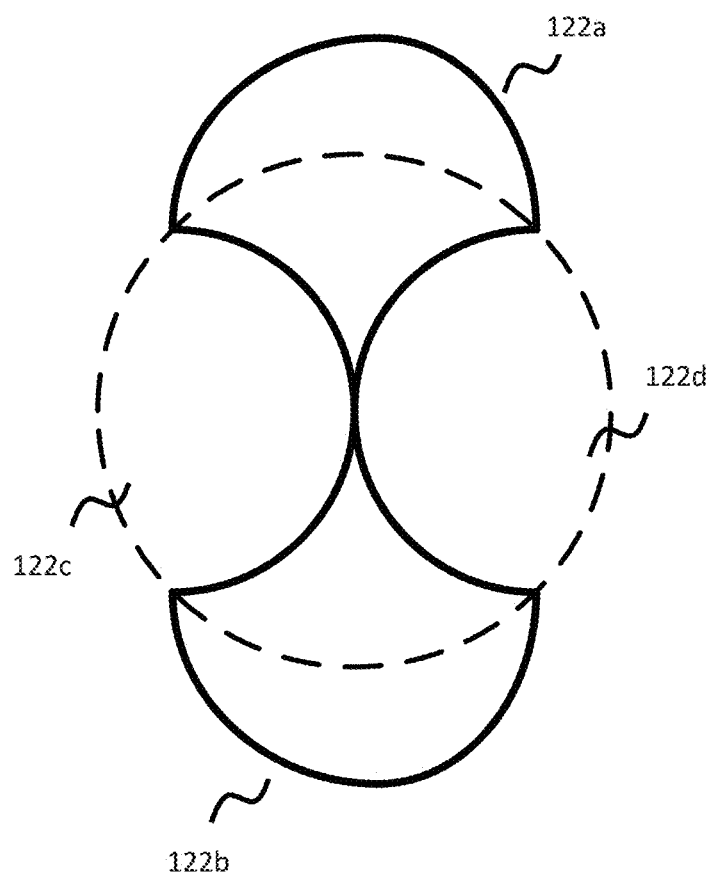
FIG. 8 shows a distal end region of the clot retrieval device of FIGS. 6 and 7, according to one embodiment.

The embodiments presented thus far generally utilize a closed distal end design, as opposed to the typical open-ended distal shape common to existing stentrievers. FIG. 6 discloses another embodiment utilizing a generally closed distal end design, but achieving this configuration in a different way. FIG. 6 shows a flat sheet thrombectomy device 130 which is laser-cut to result in a plurality of struts 102. Similar to the other embodiments, there is a first terminal region 118a configured similar to the other embodiments described earlier. This flat sheet is later placed around a tubular mandrel to impart the tubular implant device shape, a portion of this tubular final shape is generally shown in FIG. 7. The device 130 includes a number of end components 122, six (6) end components 122 are shown in FIG. 6 although fewer or more can be used. For instance, 4-24 end components can be used. Each end component 122 has a generally parabolic-type shape, though other shapes can be used in different embodiments. As shown in FIGS. 7-8, some of these end components 122 are puckered radially outward and some end components 122 are puckered radially inward—this can be done during the shape setting process by mechanically grasping these end components 122 with a gripping tool (e.g., pliers) and bending some radially inward and some radially outward. This is shown best in FIG. 8, where end components 122a-122b are puckered radially outwardly and end components 122c-122d are puckered radially inwardly.

One advantage in placing some of these end components radially inwardly is that there is a natural constriction along the distal end of the device 130 to help trap or retain clot/thrombus within the device 130. In other words, there is no complete opening along the distal end of the device. Various combinations of the end components can be placed radially inwardly or radially outwardly to affect the distal end profile (e.g., more radially inward end components would create more of a closed distal end shape). Additionally, rather than being puckered radially outwardly or radially inwardly, one or more end components can simply adopt a normal tubular configuration since that they are substantially flush with the outer portion of the tubular thrombectomy device 130 and in this way occupy a substantially flat plane. One advantage of this design is that the device can be customized to any situation by controlling the amount of end components which are inwardly oriented to create the distal constriction to help retain thrombus.

Some embodiments described herein have disclosed the use of a radiopaque element (e.g., the radiopaque coil or spring 106 of FIGS. 1-2) to aid in visualizing a clot retrieval device. The following embodiments offer other approaches of augmenting radiopacity along a clot retrieval device. These embodiments can also be combined with the radiopaque coil/spring concept shown in FIGS. 1-2 and described earlier, to further augment radiopacity, or can be used as a stand-alone concept without such inclusion of the radiopaque coil/spring concept detailed earlier.

Figure 9:
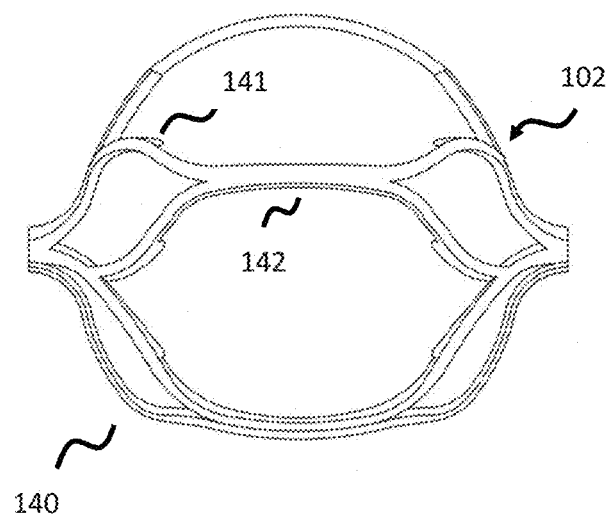
FIG. 9 shows strut elements of a clot retrieval device, according to one embodiment.

FIG. 9 shows a thrombectomy device 140, according to one embodiment, which includes a plurality of struts 102—including one or more longer configured struts 142 along the length of the device 140 and one or more shorter configured struts 141. The thrombectomy device 140 can be configured to be more elongated in shape (e.g., closer to what is shown in FIGS. 1-5), and can use various strut shape configurations. These longer configured struts 142 represent good locations where radiopacity of the device can be enhanced, since the struts 142 occupy a substantial length of the device 140.

Figure 10:
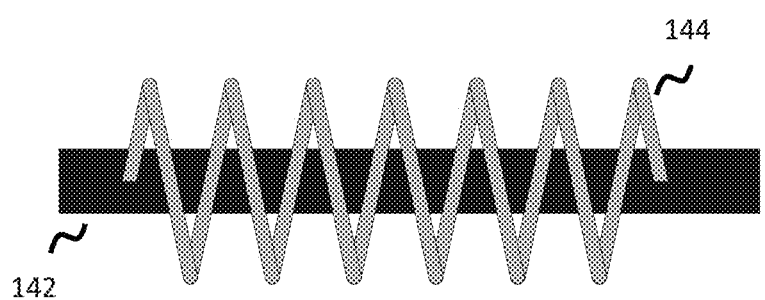
FIG. 10 shows a radiopaque coil used on a strut element of a clot retrieval device, according to one embodiment.

FIG. 10 illustrates a radiopaque element 144 which can be added to one or more struts 142 along one or more locations of each strut. In one example, the radiopaque element is a coil or spring which is placed over one or more regions of the struts 142. In one example, the radiopaque coil or spring is formed by winding a wire around the region to create a plurality of windings (e.g., two or more windings) to create the coil or spring shape—in one example, 2-3 windings are used. Any radiopaque metallic material (e.g., tantalum, platinum, palladium, gold, tungsten, or drawn-filled tubing with a radiopaque core and nitinol jacket) can be used to create the radiopaque element. In one example, the radiopaque element 144 can be placed at least along the proximal and distal end regions of struts 142 so these end regions have augmented visualization.

In one embodiment, the radiopaque element 144 is a spiral cut tube. The spiral cut tube can be created by taking a tubular element and creating a spiral cut pattern along the length of the tube, to create a plurality of nested spiral elements. With a spiral cut tube, the windings will be thicker than a coil or spring and be sized such that the thicker windings are substantially flush with each other (e.g., to give the appearance of a tube). The spiral cut tubing concept could also be used on the embodiments described earlier in regard to FIGS. 1-2, where a spiral cut tube can be used instead of a coil or spring member 106.

Figure 11:
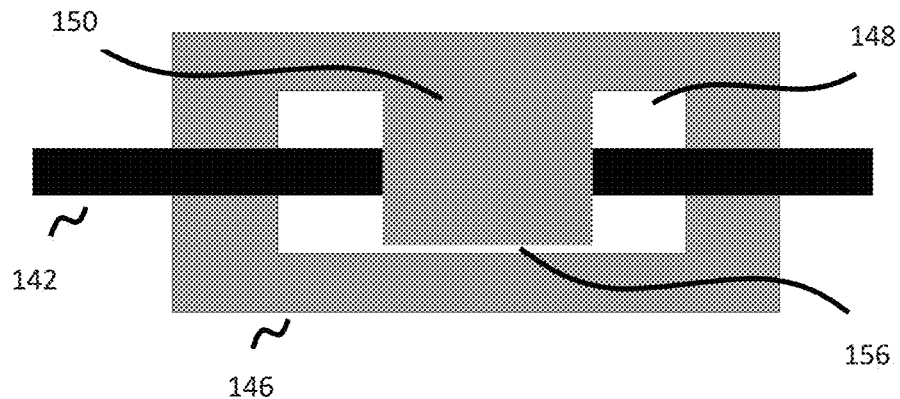
FIG. 11 shows a radiopaque plate used on a strut element of a clot retrieval device, according to one embodiment.

FIG. 11 illustrates another embodiment, which utilizes a radiopaque plating element 146, instead of a coil or spiral cut tube. The plating element 146 has a cut-out region 148. This cut out region 148 helps define a projecting surface 150 (e.g., the portion of the plating element 146 which is not cut out or removed) which is configured such that a projecting surface 150 extends over the strut component 142 while the rest of the plating element extends under the strut component 142. In this way, the strut is placed between or sandwiched between two parts of plating element 146. The plating element is welded at location 156 along the projecting surface 150 to affix the plating surface to the strut.

Figure 12:
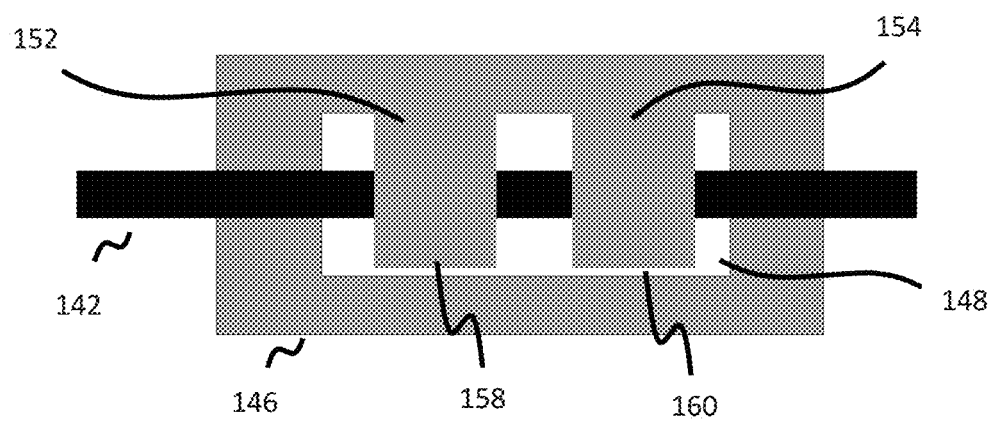
FIG. 12 shows a radiopaque plate used on a strut element of a clot retrieval device, according to one embodiment.

FIG. 12 illustrates a similar plating concept but utilizes an alternative configuration utilizing two projecting surfaces 152, 154 and two attachment locations 158, 160—instead of just one.

One advantage to the use of plating element 146 is that it can be easily assembled onto the thrombectomy device after formation and assembly of the thrombectomy device, since it is configured as a plate which is simply added to the strut. The plating element 146 can be configured in a variety of lengths and can be placed along one or more locations along strut component 142.

In another embodiment, a radiopaque tubular element (which can be referred to as a marker band) can be placed over strut regions 142 at one or more locations along the one or more elongated strut regions 142.

Figure 13:
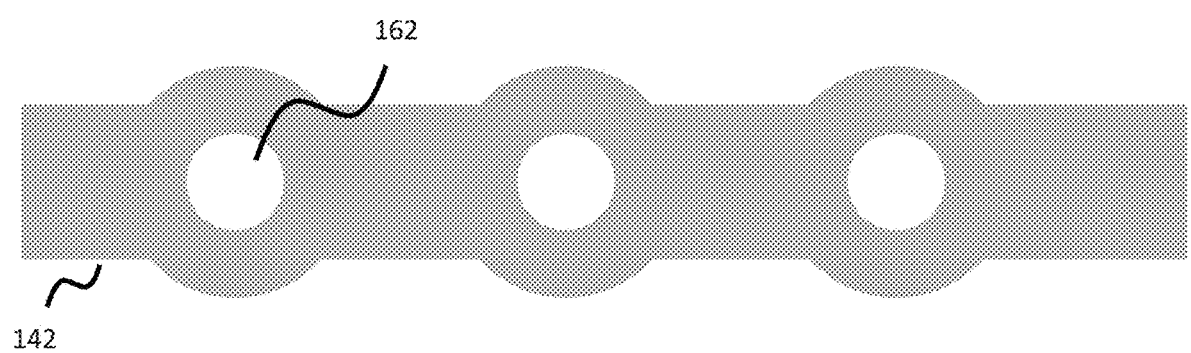
FIG. 13 shows a strut element of a clot retrieval device utilizing a coining hole, according to one embodiment.

In another embodiment, shown in FIG. 13, a strut region 142 includes one or more coining holes or slots 162. The coining holes or slots are empty spaces created along the strut region and can be made, for instance, by utilizing a hole making apparatus such as a puncturing needle or drill along selective portions of a strut region 142. In one embodiment, the hole or slot 162 is positioned completely through the width of the strut so as to form a complete hole which the radiopaque composition then fills. In another embodiment, the hole or slot 162 is only partial such that it takes the form of a superficial recess along a width of the strut but does not extend completely through the strut. The coining hole or slot 162 is then filled with a metallic radiopaque composition (e.g., tantalum, platinum, palladium, or gold). In one example, a metallic radiopaque material machined to a similar size as the coining hole so as to fit snugly within said coining hole and then placed in the hole where adhesive, welding, or other mechanical techniques can be then used to affix it. In another example, the metallic radiopaque material is melted to a liquid or gel-like state, poured or otherwise placed within the slot/hole 162, and is then left to solidify. The coining holes/slots 162 can be placed in one or more regions along a lengthier strut region 142 of the thrombectomy device, or can be placed along any strut element 102 of the device including the shorter strut regions 141. One advantage to this technique is that the overall thickness of the device will not be as affected since there is nothing being added to or physically over a strut region to enhance radiopacity.

Though the radiopacity enhancing embodiments shown in FIGS. 10-13 are sometimes described as being configured for attachment or addition to the longer strut elements 142 which extends along a significant length of the thrombectomy device 140, they can also be used along any strut element 102 of the device—including shorter strut elements 141. Furthermore, these embodiments can be used along the other thrombectomy device embodiments discussed earlier and herein (including those utilizing multiple connected thrombectomy components) in order to further augment visualization of a thrombectomy device.

What is claimed is:

1. A clot retrieval device comprising:
   a device body comprising a plurality of struts and having a medial section and tapered proximal and distal ends, the device body having a radially compressed configuration when in a delivery catheter and a radially expanded configuration when outside of the delivery catheter;
   wherein the plurality of struts define a plurality of open cells; and a coil positioned within the device body, wherein the coil applies outward force against the plurality of struts to help the device body expand from the radially compressed configuration to the radially expanded configuration, and wherein the coil is connected to a distal region and a proximal region of the device body by a pair of elongated end elements.

2. The clot retrieval device of claim 1, wherein the coil is radiopaque.

3. The clot retrieval device of claim 2, wherein the coil is composed of platinum, palladium, gold, or tantalum.

4. The clot retrieval device of claim 1, wherein the pair of elongated elements are each comprised of a wire or a tube.

5. The clot retrieval device of claim 1, wherein the coil is comprised of a wire, wherein the medial section of the device body is not tapered, and wherein the wire is positioned only within the medial section of the device body and does not extend into the tapered proximal and distal ends of the device body when the device body is in the radially expanded configuration.

6. The clot retrieval device of claim 1, the coil having an elongated configuration when the device body is in the radially compressed configuration, and an expanded configuration when the device body is in the radially expanded configuration.

7. The clot retrieval device of claim 1, wherein the tapered proximal and distal ends form closed ends.

8. A clot retrieval device comprising:
a device body comprising a plurality of struts and having a medial section and tapered proximal and distal ends, the device body having a radially compressed configuration when in a delivery catheter and a radially expanded configuration when outside of the delivery catheter;
wherein the plurality of struts define a plurality of open cells; and
a spring positioned within the device body, wherein the spring applies outward force against the plurality of struts to help the device body expand from the radially compressed configuration to the radially expanded configuration, and wherein the spring is connected to both a proximal region and a distal region of the device body by a pair of elongated end elements.

9. The clot retrieval device of claim 8, wherein the spring is radiopaque.

10. The clot retrieval device of claim 9, wherein the spring is composed of platinum, palladium, gold, or tantalum.

11. The clot retrieval device of claim 8, wherein the pair of elongated elements are each comprised of a wire or a tube.

12. The clot retrieval device of claim 8, wherein the medial section of the device body is comprised of a substantially straight-walled tubular shape, and wherein a proximal terminal end and a distal terminal end of the spring each terminate within the medial section of the device body and do not extend into the tapered proximal and distal ends of the device body when the device body is in the radially expanded configuration.

13. The clot retrieval device of claim 8, the spring having an elongated configuration when the device body is in the radially compressed configuration, and an expanded configuration when the device body is in the radially expanded configuration.

14. The clot retrieval device of claim 8, further comprising a plurality of connected device bodies.

15. The clot retrieval device of claim 8, wherein the tapered proximal and distal ends form closed ends.

16. A clot retrieval device comprising:
a device body comprising a plurality of struts and having a tubular medial section and tapered proximal and distal ends;
the device body having a radially compressed configuration when in a delivery catheter, and a radially expanded configuration when outside of the delivery catheter;
wherein the plurality of struts define a plurality of open cells; and
an inner element positioned within the device body; and, wherein the inner element radially expands and applies outward force against the plurality of struts to help prop open the device body, and wherein the inner element is connected to a distal region and a proximal region of the device body by a pair of elongated end elements.

17. The clot retrieval device of claim 16, wherein the inner element is a coil or spring.

18. The clot retrieval device of claim 17, the inner element having a substantially linear profile when the device body is in the radially compressed configuration.

19. A clot retrieval device comprising:
a device body comprising a plurality of struts and having a medial section and tapered proximal and distal ends, the device body having a radially compressed configuration when in a delivery catheter and a radially expanded configuration when outside of the delivery catheter;
wherein the plurality of struts define a plurality of open cells; and
a coil positioned within the device body, wherein the coil applies a first outward force against the plurality of struts to help the device body expand from the radially compressed configuration to the radially expanded configuration, and wherein the first outward force provides at least a portion of a total outward force that moves the device body from the radially compressed configuration to the radially expanded configuration when outside the delivery catheter, and wherein the coil is connected to a distal region and a proximal region of the device body by a pair of elongated elements.

20. The clot retrieval device of claim 19, wherein the device body is constructed at least in part by a shape memory material, and wherein the shape memory material applies a second outward force that provides at least a portion of the total outward force that moves the device body from the radially compressed configuration to the radially expanded configuration when outside the delivery catheter.

21. The clot retrieval device of claim 20, wherein the total outward force equals the first outward force plus the second outward force.

* * * * *